US00PP20418P2

(12) United States Plant Patent
Michalik

(10) Patent No.: US PP20,418 P2
(45) Date of Patent: Oct. 13, 2009

(54) ***GERANIUM* PLANT NAMED 'CAMDARED'**

(50) Latin Name: *Pelargonium grandiflorum*
Varietal Denomination: Camdared

(75) Inventor: Andrea Michalik, Dresden (DE)

(73) Assignee: Elsner PAC Jungpflanzen, Dresden (DE)

( * ) Notice: Subject to any disclaimer, the term of this patent is extended or adjusted under 35 U.S.C. 154(b) by 0 days.

(21) Appl. No.: 12/214,624

(22) Filed: Jun. 20, 2008

(51) Int. Cl.
*A01H 5/00* (2006.01)

(52) U.S. Cl. ..... Plt./331

(58) Field of Classification Search ..... Plt./331
See application file for complete search history.

(56) References Cited

OTHER PUBLICATIONS

UPOV-ROM GTITM, Plant Variety Database, 2008/06, Jouve Retrieval Software, citation for 'Camdared'.*

* cited by examiner

*Primary Examiner*—Susan B McCormick Ewoldt
(74) *Attorney, Agent, or Firm*—C. A. Whealy

(57) ABSTRACT

A new and distinct cultivar of Regal *Geranium* plant named 'Camdared', characterized by its upright, somewhat outwardly spreading and mounded plant habit; vigorous growth habit; freely basal branching habit; relatively small leaves; early and freely flowering habit; dark red and red purple bi-colored flowers; and no requirement for cooling treatment for flower development.

1 Drawing Sheet

Botanical designation: *Pelargonium grandiflorum.*
Cultivar denomination: 'Camdared'.

BACKGROUND OF THE INVENTION

The present invention relates to a new and distinct cultivar of Regal *Geranium*, botanically known as *Pelargonium grandiflorum,* and hereinafter referred to by the name 'Camdared'.

The new Regal *Geranium* is a product of a planned breeding program conducted by the Inventor in Dresden, Germany. The objective of the breeding program is to develop new Regal *Geraniums* that do not require a cooling treatment for flower development.

The new Regal *Geranium* originated from a cross-pollination made by the Inventor in Dresden, Germany during the summer of 2003 of two unnamed proprietary selections of *Pelargonium grandiflorum,* not patented. The new Regal *Geranium* was discovered and selected by the Inventor as a flowering plant from within the progeny of the stated cross-pollination in a controlled greenhouse environment in Dresden, Germany during the spring of 2004.

Asexual reproduction of the new Regal *Geranium* by vegetative terminal cuttings in a controlled greenhouse environment in Dresden, Germany since October, 2004, has shown that the unique features of this new Regal *Geranium* are stable and reproduced true to type in successive generations.

SUMMARY OF THE INVENTION

Plants of the new Regal *Geranium* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Camdared'. These characteristics in combination distinguish 'Camdared' as a new and distinct cultivar of Regal *Geranium:*

1. Upright, somewhat outwardly spreading and mounded plant habit.
2. Vigorous growth habit.
3. Freely basal branching habit.
4. Relatively small leaves.
5. Early and freely flowering habit.
6. Dark red and red purple bi-colored flowers.
7. Does not require cooling treatment for flower development.

Plants of the new Regal *Geranium* differ primarily from plants of the parent selections in flower coloration. In addition, plants of the new Regal *Geranium* are more uniform than plants of the parent selections.

Plants of the new Regal *Geranium* can be compared to plants of the *Pelargonium grandiflorum* 'Regvel', disclosed in U.S. Plant Pat. No. 17,395. In side-by-side comparisons conducted in Dresden, Germany, plants of the new Regal *Geranium* differed from plants of 'Regvel' in the following characteristics:

1. Plants of the new Regal *Geranium* were more freely flowering than plants of 'Regvel'.
2. Plants of the new Regal *Geranium* had more rounded flower petals than plants of 'Regvel'.
3. Plants of the new Regal *Geranium* and 'Regvel' differed in flower color as plants of the new Regal *Geranium* had darker-colored flowers.

BRIEF DESCRIPTION OF THE PHOTOGRAPH

The accompanying colored photograph illustrates the overall appearance of the new Regal *Geranium*, showing the colors as true as it is reasonably possible to obtain in colored reproductions of this type. Colors in the photograph may differ slightly from the color values cited in the detailed botanical description which accurately describe the colors of the new Regal *Geranium*. The photograph comprises a side perspective view of a typical flowering plant of 'Camdared' grown in a container.

DETAILED BOTANICAL DESCRIPTION

The aforementioned photograph and following observations, measurements and values describe plants grown in Dresden, Germany in a glass-covered greenhouse during the winter and spring and under conditions which closely approximate commercial Regal *Geranium* production. During the production of the plants, day temperatures averaged 18° C., night temperatures averaged 16° C. and light levels ranged from 15 kilolux to 100 kilolux. Plants were six months from planting when the photograph and the description were taken. In the detailed description, color references are made to The Royal Horticultural Society Colour Chart, 1995 Edition, except where general terms of ordinary dictionary significance are used.

Botanical classification: *Pelargonium grandiflorum* 'Camdared'.

Parentage:

*Female, or seed, parent.*—Unnamed proprietary selection of *Pelargonium grandiflorum,* not patented.

*Male or pollen parent.*—Unnamed proprietary selection of *Pelargonium grandiflorum,* not patented.

Propagation:

*Type.*—By vegetative terminal cuttings.

*Time to initiate roots, summer.*—About 18 days at temperatures of 20° C.

*Time to initiate roots, winter.*—About 22 days at temperatures of 20° C.

*Time to produce a rooted young plant, summer and winter.*—About 30 days at temperatures of 20° C.

*Root description.*—Fine, fibrous; white in color.

*Rooting habit.*—Freely branching; dense.

Plant description:

*Plant/growth habit.*—Upright, somewhat outwardly spreading and mounded plant habit; inverted triangle; densely foliated. Vigorous growth habit. Freely basal branching habit with about eight lateral branches developing per plant.

*Plant height, to top of umbels.*—About 30 cm.

*Plant height, to top of leaves.*—About 22 cm.

*Plant width.*—About 30 cm.

*Lateral branches.*—Length: About 15 cm. Diameter: About 5 mm to 8 mm. Internode length: About 2 cm to 3 cm. Texture: Pubescent. Color: Close to 144A.

Foliage description:

*Arrangement.*—Alternate or opposite; simple.

*Length.*—About 3 cm to 6 cm.

*Width.*—About 6 cm to 8 cm.

*Shape.*—Cordate; palmately lobed.

*Apex.*—Acute.

*Base.*—Cordate, open.

*Margin.*—Serrate to biserrate.

*Venation pattern.*—Palmate.

*Texture, upper surface.*—Smooth, glabrous; leathery.

*Texture, lower surface.*—Slightly pubescent on veins; leathery.

*Color.*—Developing and fully expanded foliage, upper surface: Close to 137B; venation, close to 137B. Developing and fully expanded foliage, lower surface: Close to 147B; venation, close to 146C. Zonation pattern: Not discernible. Petiole: Length: About 2 cm to 6 cm. Diameter: About 3 mm. Texture, upper and lower surfaces: Pubescent. Color, upper and lower surfaces: Close to 144A.

Flower description:

*Flower arrangement.*—Single rotate flowers arranged in inversely conical umbels arising from apical leaf axils. Umbels displayed above the foliage on strong peduncles. Flowers face upright to outward. Flowers not persistent. Flowers not fragrant.

*Quantity of flowers.*—Freely flowering habit; about three to five flowers per umbel.

*Flowering season.*—In Dresden, Germany, flowering initiates in the spring and continues throughout the summer into the autumn. Plants do not require a cooling treatment for flower development.

*Flower longevity.*—Individual flowers last about two weeks on the plant.

*Umbel height.*—About 6 cm.

*Umbel diameter.*—About 8 cm to 10 cm.

*Flower diameter.*—About 5 cm.

*Flower depth* (*height*).—About 2 cm.

*Flower buds.*—Length: About 1 cm. Diameter: About 5 mm. Shape: Roughly elliptical. Color: Close to 143B.

*Petals.*—Quantity per flower: Five; imbricate. Length, upper and lower petals: About 3.5 cm. Width, upper and lower petals: About 2 cm to 3 cm. Shape: Obovate. Apex: Rounded. Base: Cuneate. Margin: Entire. Texture, upper and lower surfaces: Smooth, glabrous; satiny. Color: When opening and fully opened, upper surface: Close to 53A; towards the base, close to 67A; venation, darker than 59A. Color becoming closer to 46A with development. When opening and fully opened, lower surface: Close to 59C; towards the base, close to 67A; venation, darker than 59A.

*Sepals.*—Quantity per flower: Five, arranged in a single whorl. Length: About 1.5 cm. Width: About 5 mm. Shape: Lanceolate. Apex: Acute. Margin: Entire. Texture, upper and lower surfaces: Pubescent. Color, upper and lower surfaces: Close to 146C.

*Peduncle* (*umbel stem*).—Length: About 5 cm. Diameter: About 2 mm. Strength: Strong. Angle: Mostly erect to slightly outwardly slanted. Texture: Pubescent. Color: Close to 146B.

*Pedicel* (*individual flower stem*).—Length: About 2.5 cm. Diameter: About 1 mm. Strength: Strong; flexible. Texture: Pubescent. Color: Close to 146B.

*Reproductive organs.*—Androecium: Stamen quantity per flower: About five to seven. Anther length: About 2 mm. Anther shape: Tubular. Anther color: Close to 162A. Pollen amount: Abundant. Pollen color: Close to 162A. Gynoecium: Pistil quantity per flower: One. Pistil length: About 1.5 cm. Stigma shape: Five to six-parted. Stigma color: Close to 71A. Style length: About 1 cm. Style color: Close to 71A. Ovary color: Close to 146C. Seeds: Seed development has not been observed on plants of the new Regal *Geranium.*

Disease/pest resistance: Plants of the new Regal *Geranium* have not been observed to be resistant to pathogens and pests common to Regal *Geraniums.*

Temperature tolerance: Plants of the new Regal *Geranium* have been observed to tolerate temperatures ranging from about 1° C. to about 35° C. to 40° C.

It is claimed:

1. A new and distinct Regal *Geranium* plant named 'Camdared' as illustrated and described.

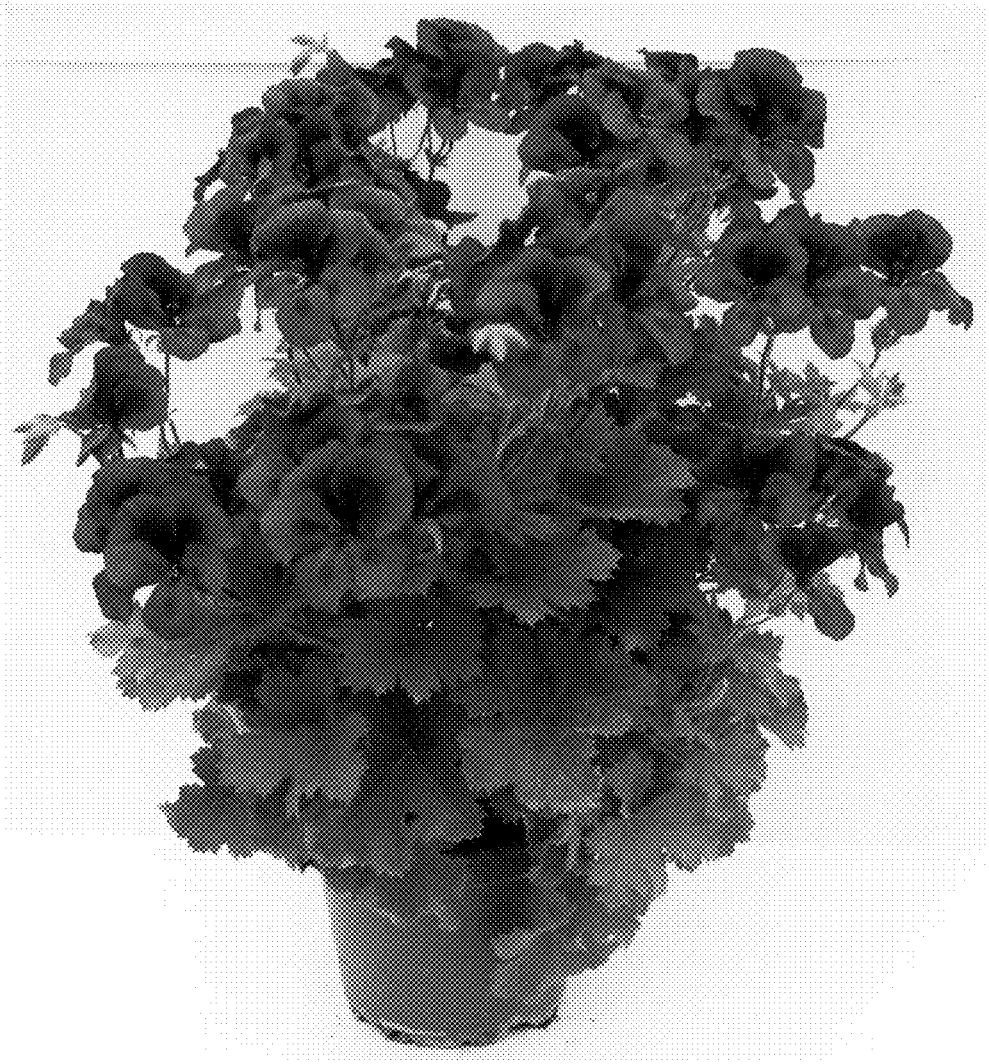

* * * * *